US012599477B2

(12) United States Patent
Schreiber

(10) Patent No.: US 12,599,477 B2
(45) Date of Patent: Apr. 14, 2026

(54) ARTIFICIAL EYE LENS

(71) Applicant: Carl Zeiss Meditec AG, Jena (DE)

(72) Inventor: Benjamin Schreiber, Berlin (DE)

(73) Assignee: Carl Zeiss Meditec AG, Jena (DE)

( * ) Notice: Subject to any disclaimer, the term of this patent is extended or adjusted under 35 U.S.C. 154(b) by 630 days.

(21) Appl. No.: 17/998,369

(22) PCT Filed: May 7, 2021

(86) PCT No.: PCT/EP2021/062172
§ 371 (c)(1),
(2) Date: Nov. 10, 2022

(87) PCT Pub. No.: WO2021/228717
PCT Pub. Date: Nov. 18, 2021

(65) Prior Publication Data
US 2023/0149154 A1 May 18, 2023

(30) Foreign Application Priority Data
May 13, 2020 (DE) .......................... 102020206037.1

(51) Int. Cl.
*A61F 2/16* (2006.01)
*A61F 2/14* (2006.01)
(52) U.S. Cl.
CPC .............. *A61F 2/1651* (2015.04); *A61F 2/15* (2015.04); *A61F 2/1645* (2015.04);
(Continued)
(58) Field of Classification Search
CPC .................. A61F 2/1613; A61F 2/1648; A61F 2250/0003; A61F 2/15;
(Continued)

(56) References Cited

U.S. PATENT DOCUMENTS 4,585,457 A * 4/1986 Kalb .................... A61F 2/1616
623/6.13
5,222,981 A 6/1993 Werblin
(Continued)

FOREIGN PATENT DOCUMENTS

DE 68912196 6/1994
DE 102007048859 4/2009
(Continued)

OTHER PUBLICATIONS

International Search Report (English translation) and Written Opinion for International Application No. PCT/EP2021/062172 date mailed Aug. 16, 2022.

*Primary Examiner* — Javier G Blanco
(74) *Attorney, Agent, or Firm* — DeWitt LLP

(57) ABSTRACT

An eye lens having a front lens element and a rear lens element, which each have a positive optical power and an optical region, and an intermediate element, which is connected to the lens elements outside the optical regions so that the lens elements and the intermediate element form a cavity. The eye lens allows the width of an access incision necessary for implantation to be reduced. The eye lens includes the lens elements and the intermediate element that are shaped such that, in the implanted state, a distance between the front lens element and the rear lens element is fixed and the cavity has an opening which allows liquid to flow into the cavity. Embodiments of the invention include a method for producing such an eye lens and a method for implantation.

15 Claims, 4 Drawing Sheets

(52) U.S. Cl.
CPC . *A61F 2002/1681* (2013.01); *A61F 2240/001*
(2013.01); *A61F 2250/0003* (2013.01)

(58) Field of Classification Search
CPC .. A61F 2002/169053; A61F 2002/1681; A61F
2/1601; A61F 2/1651
See application file for complete search history.

(56) References Cited

U.S. PATENT DOCUMENTS

| | | | | |
|---|---|---|---|---|
| 5,354,335 | A | 10/1994 | Lipshitz et al. | |
| 5,405,387 | A * | 4/1995 | Sodero | A61F 2/1613 |
| | | | | 623/6.13 |
| 8,579,970 | B1 | 11/2013 | Zadno-Azizi et al. | |
| 9,427,312 | B2 | 8/2016 | Deboer et al. | |
| 2002/0107568 | A1* | 8/2002 | Zadno-Azizi | A61F 2/1629 |
| | | | | 623/6.37 |
| 2003/0018384 | A1 | 1/2003 | Valyunin et al. | |
| 2004/0236421 | A1* | 11/2004 | Lipshitz | A61F 2/1613 |
| | | | | 623/6.34 |
| 2006/0265059 | A1 | 11/2006 | Sunada et al. | |
| 2007/0201138 | A1 | 8/2007 | Lo | |
| 2011/0060408 | A1* | 3/2011 | Tsai | A61F 2/16 |
| | | | | 623/6.62 |
| 2011/0153014 | A1* | 6/2011 | Zhang | A61F 2/1624 |
| | | | | 623/6.34 |
| 2011/0279905 | A1 | 11/2011 | Pugh et al. | |
| 2015/0216652 | A1* | 8/2015 | Jansen | A61F 2/16 |
| | | | | 623/6.43 |
| 2015/0238309 | A1 | 8/2015 | Jansen | |
| 2016/0058553 | A1* | 3/2016 | Salahieh | A61F 2/1629 |
| | | | | 623/6.13 |
| 2016/0235523 | A1* | 8/2016 | Borja | A61F 2/1648 |
| 2016/0317287 | A1 | 11/2016 | Silvestrini et al. | |
| 2019/0125523 | A1 | 5/2019 | Barzilay | |

FOREIGN PATENT DOCUMENTS

| | | | | |
|---|---|---|---|---|
| DE | 202010010365 | 3/2011 | | |
| EP | 3273294 | 1/2018 | | |
| FR | 2666735 | 3/1992 | | |
| WO | WO9520926 | 8/1995 | | |
| WO | WO9936004 | 7/1999 | | |
| WO | WO-0004849 A1 * | 2/2000 | | A61F 2/1627 |
| WO | WO9911303 | 6/2000 | | |
| WO | WO2008101522 | 8/2008 | | |
| WO | WO2011065986 | 6/2011 | | |
| WO | WO2014029383 | 2/2014 | | |
| WO | WO2014121391 | 8/2014 | | |
| WO | WO2017181295 | 10/2017 | | |

* cited by examiner

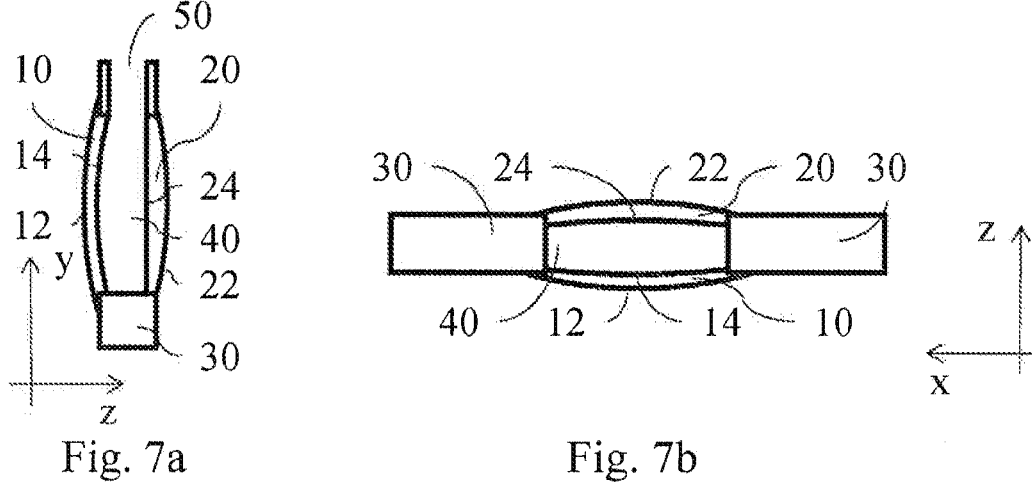
Fig. 7a                     Fig. 7b
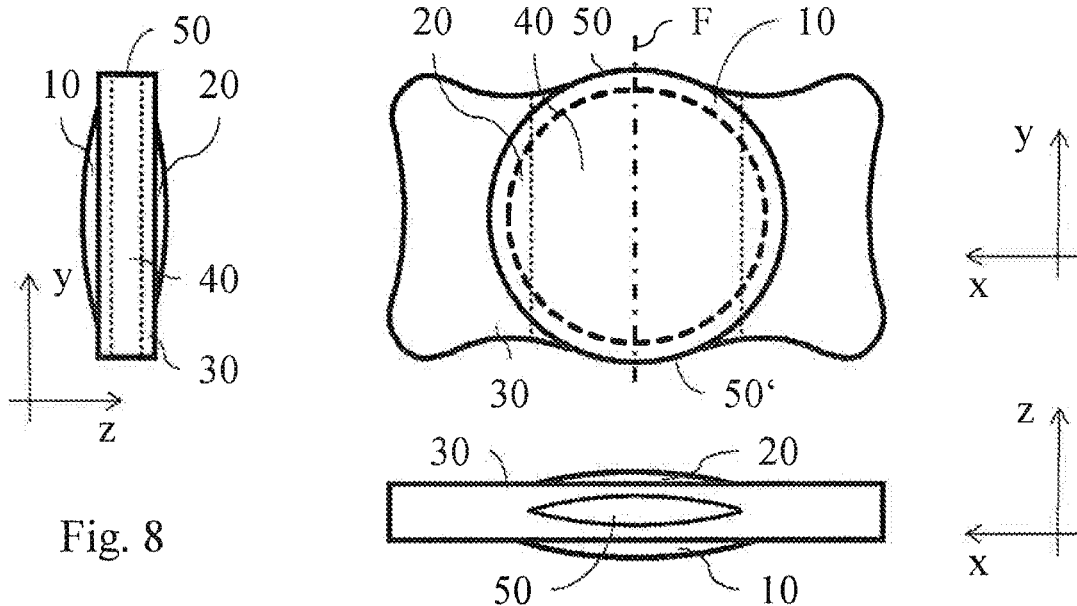
Fig. 8
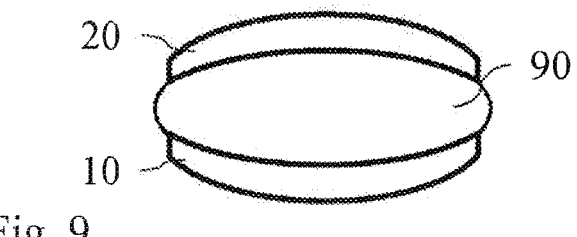
Fig. 9

ARTIFICIAL EYE LENS

RELATED APPLICATIONS

This application is a National Phase entry of PCT Application No. PCT/EP2021/062172, filed May 7, 2021, which application claims the benefit of priority to DE Application No. 10 2020 206 037.1, filed May 13, 2020 the entire disclosures of which are incorporated herein by reference

TECHNICAL FIELD

Example embodiments of the invention relate to intraocular lenses to be implanted into an eye.

BACKGROUND

Example embodiments of the invention relate to an eye lens for implantation in an eye, comprising a front lens element having a first optical region and a first positive refractive power, a back lens element having a second optical region and a second positive refractive power, and comprising an intermediate element, wherein the intermediate element is connected to the front lens element outside the first optical region and to the back lens element outside the second optical region, so that the front lens element, the back lens element, and the intermediate element form a cavity. The invention further relates to a method for producing such an eye lens. Finally the invention relates to a method for implanting such an eye lens.

The use of artificial eye lenses or intraocular lenses (IOLs) has become established for the treatment of a cataract. In the process, the crystalline lens that has been opacified by the cataract is removed and replaced by an intraocular lens. However, the use of an artificial eye lens may also be necessary for other reasons. For example, optical concepts have recently been implemented that enable the correction of presbyopia and/or correct astigmatism. Typically, use is made of intraocular lenses which have one or more fixed focal lengths and thus enable one or more fixed focal positions in the implanted state. A clump in the focal position depending on forces within the eye, which may be caused, for example, by the ciliary muscle of the eye, is not desirable.

A plurality of intraocular lenses are implanted in the capsular bag of an eye. To this end, the anterior capsular bag membrane is opened, the crystalline lens is comminuted and removed, and the artificial eye lens is inserted into the remaining capsular bag. In the process, the intraocular lens is inserted via a so-called access incision, which provides an opening through the cornea into the capsular bag. The width of the access incision affects subsequent wound healing and possible complications during implantation. Furthermore, the width has an influence on the stability of the eye. If this is severely impaired by the access incision, this may affect the refractive powers of the optically effective areas of the eye (such as the cornea). This may lead to the refractive power of the implanted eye lens no longer leading to the desired vision in the eye. In addition, astigmatism may be induced as a result of the implantation. It is therefore important to keep the width of the access incision as small as possible. Nowadays, widths of less than 2 mm are required for access incisions within the scope of what is known as "micro-incision cataract surgery" (MICS). The intraocular lenses used in this case are folded before implantation into the eye and inserted into the eye using a special injector. Materials for an optical lens material, which is suitable fir the optical part of an intraocular lens and at the same time is soft enough for the lens to be folded, are presented in example fashion in EP 1 009 450 A1.

SUMMARY OF THE INVENTION

Example embodiments of the present invention describe an eye lens that allows the width of access incisions to be further reduced.

A first aspect of the invention relates to an eye lens for implantation in an eye, comprising a front lens element having a first optical region and a first positive refractive power, and comprising a back lens element having a second optical region and a second positive refractive power. In the implanted state, the front lens element faces the cornea of the eye and the back lens element faces the retina. The two optical regions of the respective lens elements are designed such that light can enter the lens element on the respective cornea-facing side of the optical region and exit the lens element on the respective retina-facing side of the optical region. The aforementioned sides are designed as optical surfaces and are also called optically effective surfaces. The optical region of a lens element can therefore be penetrated by light in the implanted state of the eye lens and contributes to imaging on the retina. To realize the positive refractive powers, the lens elements can be biconvex, plano-convex or designed as a meniscus lens. The optical surfaces of the lens elements can be spherical or aspherical in shape. Furthermore, they can adopt the form of a free-form surface, that is to say they can, for example, be described by a polynomial or be described piecewise by polynomials. The optical surfaces can additionally comprise diffractive optical structures in order to provide more than one refractive power, for example.

The eye lens furthermore comprises an intermediate element. The latter is securely connected to the front lens element outside the first optical region and to the back lens element outside the second optical region. In the implanted state, the front and the back lens element are not interconnected in the first and second optical region. Thus, the front lens element, the back lens element, and the intermediate element form a cavity. According to the invention, the front and the back lens element and the intermediate element are shaped in such a way that in the implanted state the spacing of the front lens element from the back lens element is fixed; they are then at a fixed distance from one another. To this end, the aforementioned elements have a stability or stillness that cannot be deformed by typical forces within the eye, which can be caused, for example, by the ciliary muscle of the eye. By way of example, the forces can be transmitted to the intermediate element via a haptic element, by use of which the eye lens is held and positioned in the eye, or via other boundaries of the eye lens. In the implanted state, the distance between the front and the back lens element changes by less than 20%, for example less than 10%, in another example less than 5%. The front and the back lens element have a fixed (positive) refractive power in the implanted state. To this end, the lens elements and the intermediate element may for example consist of known and established materials, from which non-accommodating intraocular lenses are typically manufactured. As a result of the fixed distance between the lens elements and their fixed refractive powers, it is ensured in the implanted state that the total refractive power of the eye lens, which results from the refractive powers of the lens elements and their distance from one another, is already known before the implantation (taking into account the refractive indices of the media surrounding the lens elements). Exact knowledge of the total refractive power of the eye lens allows a precise selection of the eye lens for the respective eye. In addition, the intermediate element can also be shaped in such a way that the relative positions of the lens elements are fixed in relation to one another in the implanted state. In this way, tilting or twisting of the lens elements relative to one another can be prevented, which could otherwise also change the overall refractive power or produce image aberrations. The presented eye lens according to the invention is therefore a non-accommodating artificial eye lens.

Furthermore, according to the invention, the cavity made up of the front lens element, back lens element, and intermediate element has an opening which allows liquid to flow into the cavity. A boundary of the opening can include surfaces of the lens elements and/or of the intermediate element. Dimensions of the boundary can deviate from the distance between the lens elements. The opening allows the eye lens to be compressed prior to implantation, in such a way that the cavity has only a small volume. Following the implantation, liquid (e.g., aqueous humor) can flow into the cavity, and so only then does the eye lens take its final shape and is the distance between the lens elements fixed. As a result of the reduced volume of the cavity prior to implantation, the eye lens according to the invention can be inserted into the eye via an injector that requires a smaller width for the access incision than is possible according to the prior art. In addition, the forces required to compress the eye lens for an injection are lower, and so the injection into the eye can also be carried out with a lower injection force. This can reduce the risk of complications during implantation. The eye lens according to the invention thus advantageously makes it possible to reduce the risks of an IOL implantation for the patient and to maintain the stability of the eye, and thereby to avoid an incorrect adjustment of the refractive power by way of the artificial eye lens.

The at least four optically effective surfaces of the eye lens according to the invention enable additional degrees of freedom in the optical design with respect to an eye lens with only two optically effective surfaces. This makes it easier to correct aberrations. Chromatic aberrations can additionally be corrected if, for example, materials with different refractive indices are used for the front and the back lens element.

In a particularly advantageous configuration, the front and the back lens element are designed so that the eye lens can be folded. For this purpose, the two lens elements have a stillness that, on the one hand, is so great that no deformation can occur due to forces within the eye and, on the other hand, still allows folding of the eye lens prior to implantation, for example by use of an injector. By folding the eye lens, it is possible to carry out an implantation via access incisions with a particularly small width.

The eye lens can be folded particularly well if the cavity has two openings that are opposite one another. For example, in a rectangular coordinate system with a z-axis pointing in the direction of an optical axis of the eye lens, the two openings may have the same x-values or the same y-values. The two openings form a type of slit in the intermediate element connecting the two lens elements. Folding the eye lens along the imaginary connection between the two openings enables a particularly compact shape of the eye lens for implantation. The cavity can also have more than two openings, which are arranged, for example, rotationally symmetrically with respect to a center of the cavity.

After implantation of the eye lens, the cavity is typically filled with a liquid that has a lower refractive index than the refractive indices of the lens elements. While the refractive index, of the lens elements can typically be around 1.4 to 1.5, the refractive index of aqueous humor, for example, is around 1.33. Surprisingly, this fact makes it possible to reduce the thickness of an artificial eye lens in comparison with an eye lens according to the prior art that has the same refractive power. In this context, the thickness of the eye lens is to be understood as meaning its maximum extent along the z-axis. Typically, the maximum extent occurs between the lens vertex of the cornea-facing surface of the front lens element and the retina-facing surface of the back lens element.

If the lens elements have, for example, flat surfaces on the sides facing the cavity, then the cavity acts like a plane-parallel plate with a lower refractive index with respect to the lens elements. For an eye lens according to the invention with such a cavity, this results in a focal length that is shorter than for an eye lens without a cavity. Due to the relationships of the refractive indices in the cavity and the lens elements, which are exactly the opposite of that of a plane-parallel glass pane in air, which lengthens a focal length, the resulting effect is also exactly the opposite here. As a result, the focal point of light incident on the front lens element in parallel is closer to the vertex of the retina-facing surface of the back lens element than in the case of an eye lens without a cavity but with the same surface curvatures of the cornea-facing and retina-facing surfaces, respectively. Surprisingly, this effect thus makes it possible to achieve a higher refractive power for an eye lens of the same thickness (as for an eye lens according to the prior art). Furthermore, an eye lens with the same refractive power can be realized, with the cornea-facing and retina-facing surfaces of the front and the back lens element, respectively, having a smaller curvature; as a result, the eye lens according to the invention can have a smaller thickness than an eye lens according to the prior art with the same refractive power. It should be noted that the explanations also apply to lens elements with a positive refractive power that do not have plane surfaces on the side facing the cavity.

Thus, in an advantageous configuration, the eye lens has a thickness of less that 3 mm, for example less than 1.5 mm, in another example less than 0.9 mm. Such an eye lens therefore has a smaller thickness than is currently possible according to the prior art. This is particularly advantageous for eye lenses that are intended to provide a high overall refractive power. A cavity with a large thickness (extent in the z-direction) is particularly advantageous in this case.

According to an advantageous configuration of the eye lens, a surface which is part of the front and/or back lens element and which faces the cavity comprises a coating which prevents the front and the back lens element from sticking together. If an eye lens is compressed or folded for an injection into the eye, there may be contact between the surfaces of the lens elements facing the cavity. The coating ensures that the two surfaces separate again after implantation. The coating can be heparin, for example. In this way, the desired total refractive power of the eye lens post implantation can be ensured. This is particularly advantageous for an eye lens that can be folded, since contact of the aforementioned surfaces during an injection is particularly likely in this case.

In a particularly advantageous configuration of the eye lens, a surface which is part of the front and/or back lens element and which faces the cavity comprises a stop. With the aid of a stop, it is possible, for example, to influence the angular spectrum of light incident on the retina. This allows the perceived depth of field to be adjusted, for example. To this end, the stop may have an annular configuration.

In addition or as an alternative, a surface which is part of the front and/or back lens element and which faces the cavity comprises a diffractive optical structure. A diffractive optical structure should be understood to mean an interface between two media with different refractive indices (for example lens material of the lens element and aqueous humor) designed such that light is diffracted when passing through the interface and interferes constructively. Typically, the surface has a edge and consequently has a discontinuity in the gradient of the interface at these edges. The diffractive optical structure can be arranged rotationally symmetrically—for example in relation to the optical axis of the eye lens. The diffractive optical structure can also be superimposed on a curved surface. In this case, the structure can be "missing" from or placed on top of this curved surface. The diffractive optical structure makes it possible, for example, to provide more than one refractive power.

According to a particularly advantageous configuration, the front and/or the back lens element each have exactly two optically effective surfaces. This means that the optically effective surfaces of the front lens element consist of the cornea-facing surface and the cavity-facing surface. In addition or as an alternative, the optically effective surfaces of the back lens element consist of the retina-facing surface and the cavity-facing surface. An eye lens designed thus is easier to manufacture than one that has further optically effective surfaces.

In a further advantageous configuration, the front and/or back lens element has an optically effective surface that is toric in shape. This can be a surface with a cylindrical, a spherical-toric or an aspherical-toric shape. With the aid of an eye lens shaped thus, it is possible to correct astigmatic errors in the eye. In an example embodiment, a cavity-facing optically effective surface has a toric shape. In this way, the surfaces of the lens elements that face the capsular bag can be shaped to be rotationally symmetric. This corresponds more to the conditions in a crystalline lens. Furthermore, the manufacture of an eye lens element with a rotationally symmetric shape on the side facing away from the cavity and a cylindrical surface on the side facing the cavity is easier than the manufacture of an eye lens surface that has different curvatures in two axes.

According to an advantageous configuration, the eye lens is formed in one piece. All parts of the eye lens are consequently made from the same material from a single workpiece (lens blank); the eye lens is not composed of several parts. Manufacturing tolerances can be better controlled by way of a one-piece eye lens, since errors when assembling individual parts of the eye lens can be avoided.

In a further advantageous configuration, the cavity is shaped so as to accommodate a clear, hydrophilic gel following the implantation of the eye lens. This can be hydrogel or silicone hydrogel, for example. Corresponding materials are established for applications on and in the eye. The stability of the eye lens can be improved by accommodating a gel in the implanted state. In this case, for example, the connection between the intermediate element and the front and/or back lens element can be softer, since the fixed distance between the lens elements only needs to be ensured by way of the gel in the cavity. In addition, swelling of the gel (hydration) can be taken into account. In addition, the distance between the lens elements can be controlled by way of controlled swelling of the gel via a targeted emission of light onto the gel. If the gel is used to improve stability, the eye lens itself may comprise fewer supporting structures and thus have a further reduced volume for implantation. Furthermore, with precise knowledge of the refractive index of the gel, the optical properties of the eye lens can be precisely adapted to the needs of the eye. For example, use is made of a gel with a lower refractive index than the lens elements should the cavity have a concave surface—i.e., the front and/or back lens element has a biconvex shape. Conversely, use is for example, made of a gel with a higher refractive index than the lens element should the cavity have a convex surface—the front and/or back lens element is in the form of a meniscus lens with a positive refractive power, with the concave side facing the cavity. In both cases, the total refractive power of the eye lens can be increased without changing the thickness of the eye lens.

For cavities that are toric (i.e., one of the cavity-facing surfaces of the front or back lens element has a toric shape), the power of the torus and the sign of the torus can be determined by way of the refractive index of the gel.

Moreover, the gel allows a reduction in possible light scattering within the cavity or other possible side effects such as the appearance of bubbles. Furthermore, a medicament or other chemicals which, for example, are administered in a targeted manner over a relatively long period of time can be introduced into the eye via the gel.

The gel can be introduced into the cavity via an applicator through the access incision and the opening of the cavity. To accommodate the clear, hydrophilic gel, the cavity can, for example, be shaped in such a way that the shape of the opening is adapted to the shape of an applicator tip (like a key and lock) so that it is possible to ensure targeted administering of the gel into—and not past—the cavity. In addition or as an alternative, the cavity can have a further opening through which liquid such as aqueous humor that is already in the cavity can flow out. This further opening can be very small, so that liquid can easily flow out, while passage of gel is inhibited.

A second aspect of the invention relates to a method for producing an eye lens, in particular an eye lens according to one of the aforementioned configurations. According to the invention, the method for shaping a cavity with an opening has a method step of selective laser etching (SLE). Ultrashort laser pulses are focused into the volume of the eye lens in the process, and so the pulse energy is absorbed there at the focal point in a multi-photon process. At the focal point, the material of the eye lens is changed in such a way that it can be chemically etched there. By adjusting the focal point in the eye lens, it is possible to modify a coherent region in such a way that it can be detached using a wet-chemical process. In this way, the cavity and the opening can be worked out of a lens, blank. Other parts of the eye lens (such as the retina-facing or cornea-facing surfaces of the lens elements, or the haptic) can be produced beforehand or afterwards using known and established methods such as a turning method, for example.

In addition or as an alternative, the production method of the eye lens for shaping the cavity and the opening includes the method step of ablating an eye lens material. A drill can be used for this purpose, for example. Alternatively, the ablation can be carried out using a laser. The ablation is advantageously carried out perpendicular to the optical axis (z-axis). In the process, it is possible to carve out first the opening and then cavity. To this end, the opening advantageously has the same extent as (or a smaller extent than) the cavity in the z-direction. This is a particularly well-suited method of shaping the cavity if the surfaces of the lens elements facing the cavity are flat or cylindrical. Ablation can then be carried out in the direction of the cylinder axis.

Here, too, other parts of the eye lens can be produced beforehand or afterwards using known and established methods.

In addition or as an alternative, the production method of the eye lens for shaping the cavity and the opening includes the method step of punching. In the process, lens material is removed from the lens blank with the help of a stamp. Here, too, other parts of the eye lens can be produced beforehand or afterwards using known and established methods.

In addition or as an alternative, the production method of the eye lens for shaping the cavity and the opening includes the method step of shaping by ion implantation. In the process, impurity atoms are introduced into the eye lens in a targeted manner. The material properties of the eye lens at the site of the impurity atoms are changed by the impurity atoms in such a way that the etchability changes. For example, lens material can be detached using a wet-chemical process, thus forming the cavity. Here, too, other parts of the eye lens can be produced beforehand or afterwards using known and established methods.

In addition or as an alternative, the production method of the eye lens for shaping the cavity and the opening includes the method step of casting. For this purpose, the negative used for casting includes the cavity and the opening, and so these can be shaped in the casting process. For this purpose, the opening is for example shaped similarly to an ablating shaping of the cavity and opening so that it is easier to detach the eye lens from the negative. Other parts of the eye lens can also be produced in the casting method; they can also be subsequently produced from the cast lens blank with cavity and opening using known and established methods.

One-piece eye lenses can also be manufactured using all of the aforementioned methods. In order to manufacture an eye lens not in one piece, the manufacturing method for shaping the cavity and the opening additionally or alternatively has a method step of bracing. In this case, a force-fit connection between intermediate element and the front and/or back lens element is established by pressing together. Here, too, other parts of the eye lens can be produced beforehand or afterwards using known and established methods.

A third aspect of the invention relates to a method of implanting an eye lens comprising a cavity shaped to accommodate a clear, hydrophilic gel after the eye lens has been implanted into the eye. According to the invention, the method comprises inserting the eye lens into the eye. On account of the embodied configurations of the eye lens, the latter can be compressed particularly well for insertion into the eye, and so only a small width is required for an access incision. Furthermore, the implantation method comprises the step of introducing clear, hydrophilic gel into the cavity. The gel can be introduced using an applicator, the tip of which is inserted into the eye via the access incision and moved to the opening in the eye lens. Optionally, the applicator tip can be placed against a suitably shaped opening, in the eye lens such that the gel can be introduced into the cavity in a targeted manner.

It is understood that the features mentioned above and the features still to be explained below can be used not only in the specified combinations but also in other combinations or on their own without departing from the scope of the present invention.

BRIEF DESCRIPTION OF THE DRAWINGS

The invention is explained in greater detail below for example with reference to the accompanying drawings, which also disclose features essential to the invention. In the drawing:

FIGS. 7a and 7b are schematic illustrations of a seventh example embodiment with toric surfaces in two different sectional planes;

FIG. 8 are schematic illustrations of an eighth example embodiment with toric surfaces in a top view and in two side views; and FIG. 9 is a schematic illustration of the lens elements for a variant of the eye lens with a gel in the cavity.

DETAILED DESCRIPTION

Figures 1A, 1B, 2, 3A, 3B:
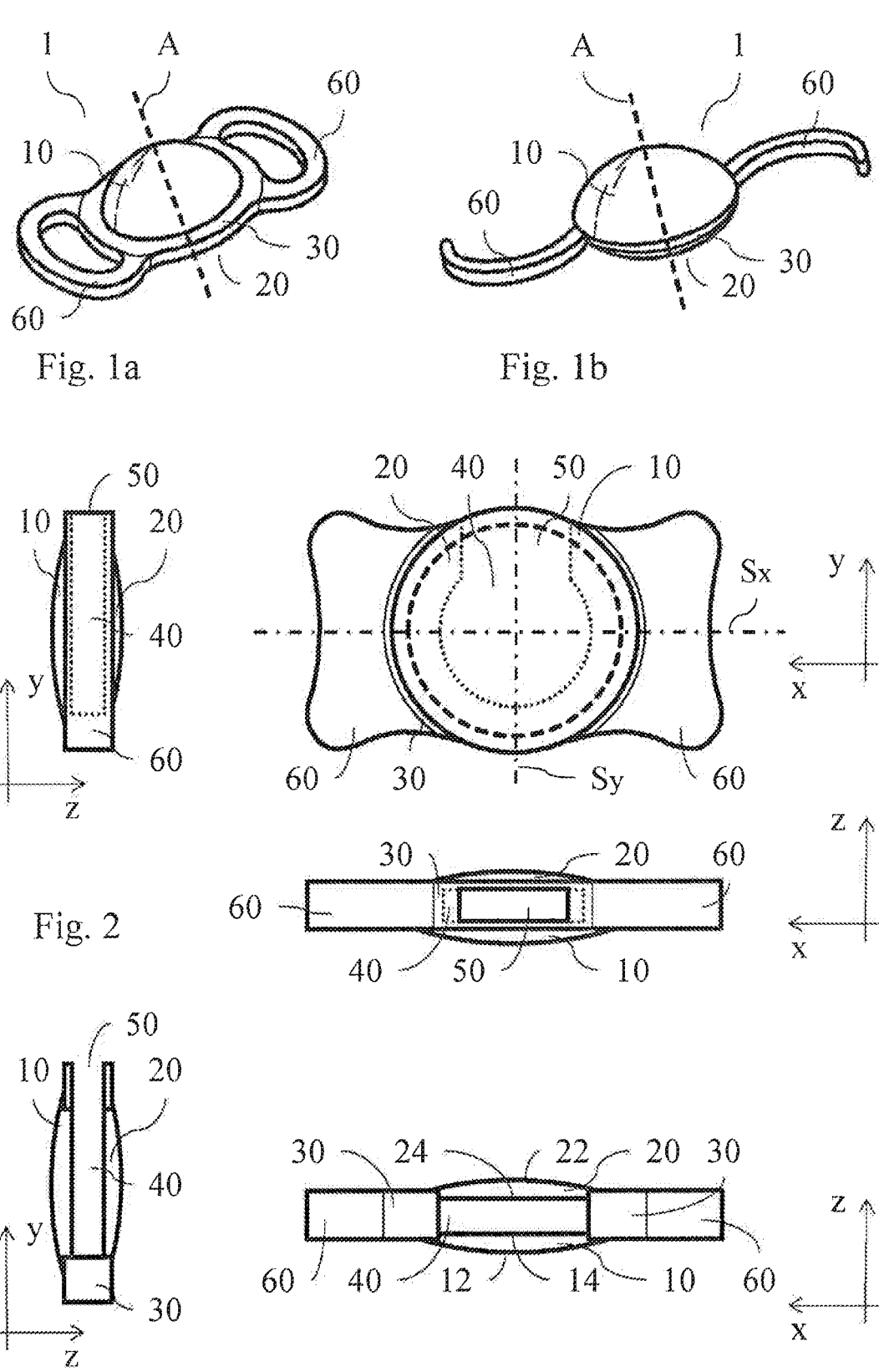
FIG. 1a depicts a perspective illustration of a first example embodiment of an eye lens according to the invention.
FIG. 1b is a perspective illustration of a further example embodiment of an eye lens.
FIG. 2 is schematic illustrations of a third example embodiment of an eye lens in a top view and in two side views.
FIGS. 3a and 3b are schematic illustrations of the third example embodiment in two different sectional planes.

FIG. 1a is a perspective illustration of a first example embodiment of an eye lens 1 according to the invention, which is designed for implantation in the capsular bag. The eye lens comprises a front lens element 10 and a back lens element 20 which is hidden in this perspective illustration. An intermediate element 30 is connected to both lens elements 10, 20. A cavity located between the lens elements and an opening are not drawn in this illustration. The intermediate element 30 is connected to two opposing haptic elements 60; in this example, these are shaped as a so-called plate haptic. The eye lens 1 is held in the eye in the implanted state by operation of the haptic elements 60. The optically effective surfaces of the front lens element 10 (and the first optical zone, not shown) and back lens element 20 (and the second optical zone, not shown) are responsible for the optical imaging properties of the eye lens 1. An optical axis A is perpendicular to an imaginary plane that is located between the cornea-facing surface of the front lens element 10—in the implanted state—and the retina-facing surface of the back lens element 20.

FIG. 1b shows a perspective illustration of a further example embodiment of an eye lens 1. It differs from the embodiment in FIG. 1a in that the haptic elements 60 are shaped, as so-called C-loops.

FIG. 2 shows a schematic illustration of a third example embodiment of an eye lens 1 according to the invention in a top view (top right) and in two side views (left and bottom). The z-direction corresponds to a view onto the eye lens 1 along the optical axis. The x- and y-directions are perpendicular thereto and perpendicular to each other. It should be noted that the illustrations here and in the other figures are not to scale. The top view (top right) shows the eye lens 1 from the z-direction. The front lens element 10 emerges from the plane of the drawing, while the back lens element 20 lies behind the plane of the drawing. The boundary of the back lens element 20 is therefore drawn as a dashed line; the radius of the back lens element 20 is smaller than that of the front lens element 10, whose boundary is represented by a solid line. The intermediate element 30 has an even larger radius; the outer edge is marked with a thin solid line. The inner edge of the intermediate element 30 is below the front lens element 10 and is marked as a dotted line. The (approximately) circular portion forms the boundary of the cavity 40 in the xy-direction. The shape of the intermediate element 30 ensures that it is connected to the lens elements 10, 20 outside the optical regions (not shown) of the said lens elements. The opening 50 is marked in the xy-plane by two dotted lines which extend to the outer edge of the lens elements 10, 20 and intermediate element 30. If the eye lens 1 is compressed for an implantation, liquid can flow into the cavity 40 through the opening 50 in the (negative) y-direction after the implantation. In the x-direction, the intermediate element 30 is connected on both sides to a respective haptic element 60 which is shaped as a plate haptic in this example embodiment.

The side view of the eye lens 1 shown on the left side of FIG. 2 corresponds to a view in the x-direction. Since the cavity 40 and the opening 50 are also located within the eye lens 1 in this view, they are represented by dotted lines. The two surfaces of the lens elements 10, 20 facing the cavity 40 are designed as flat surfaces.

A side view of the eye lens 1 from a y-direction is shown in the lower part of FIG. 2. In this view, the opening 50 is above the plane of the drawing; the opening 50 is therefore represented by a solid line.

To clarify the geometric relationships in the center of the eye lens, FIGS. 3a and 3b show, in two different sectional planes, schematic illustrations of the third example embodiment shown in FIG. 2. Here, FIG. 3a shows a section of the eye lens 1 in the yz-plane for an x-coordinate, which is marked $S_y$ in FIG. 2. Here, the opening 50 has an extent (thickness) in the z-direction which corresponds to the extent of the cavity 40 in the z-direction. This is the distance between the front lens element 10 and the back lens element 20.

FIG. 3b shows a section of the eye lens 1 in the xz-plane for a y-coordinate, which is marked $S_x$ in FIG. 2. The representations for the two sectional planes clarify the volume of the cavity 40. This volume of the eye lens 1 can be compressed for an implantation, and so the eye lens 1 can be introduced via an access incision with a particularly small width.

Figures 4A, 4B, 4C:
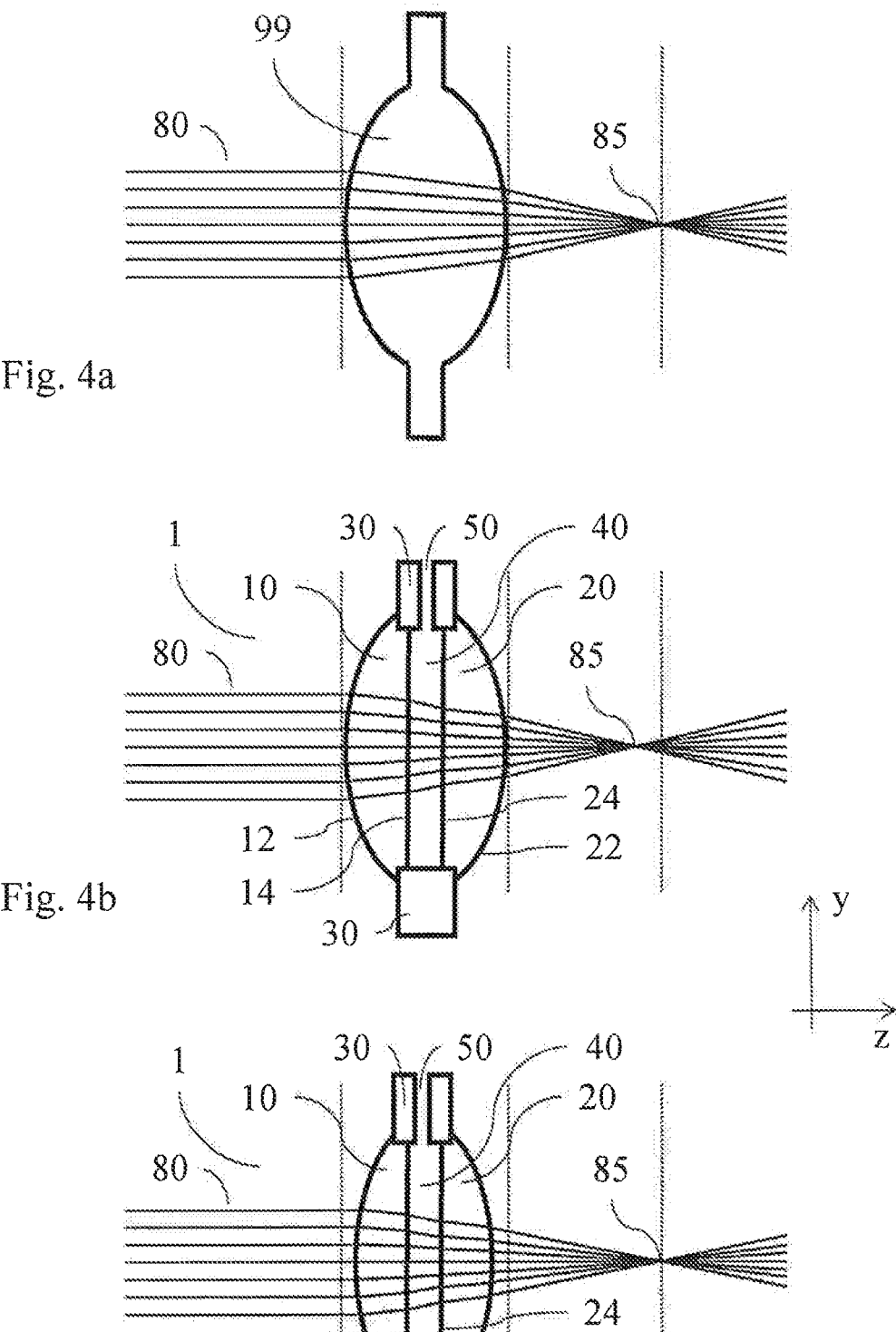
FIGS. 4a, 4b and 4c are schematic illustrations of the focal length for an eye lens according to the prior art and for a fourth and a fifth example embodiment.

FIGS. 4a, 4b and 4c depict how the volume of the eye lens 1 according to the invention is reduced in comparison with an eye lens according to the prior art. To this end, FIG. 4a shows a schematic representation of the focal length of an eye lens 99 according to the prior art in a sectional image in the yz-plane for comparison purposes. A light beam 80 incident in parallel strikes a front side (facing the cornea) of the eye lens 99, is refracted there, passes through the eye lens 99, and exits again at a back side (facing the retina). Due to the curvatures of the front side and back side, the light is focused at a focal point 85. The focal point has a focal length. The z-positions of the vertices of the eye lens 99 and of the focal point 85 are marked using dotted lines.

Analogously, FIG. 4b shows the course of an incident parallel light beam 80 for an eye lens 1 according to the invention according to a fourth example embodiment. The cornea-facing surface 12 of the front lens element 10 and the retina-facing surface 22 of the back lens element 20 have the same curvatures as the eye lens 99 according to the prior art from FIG. 4a. The surfaces 14, 24 of the lens elements 10, 20 facing the cavity 40 are plane-parallel. The lens elements

10, 20 have the same refractive index as the eye lens 99 according to the prior art. For the purposes of representing the path the light takes, it was assumed that the cavity 40 is filled with aqueous humor, which has a lower refractive index than the lens elements 10, 20. The cavity 40 acts like a plane-parallel plate with a lower refractive index with respect to the lens elements 10, 20. This results in a focal length for eye lens 1 that is shorter than for the eye lens 99 according to the prior art without the cavity 40: The focal point 85 of light incident on the front lens element 10 in parallel is located closer to the vertex of the retina-facing surface 22 of the back lens element 20 than in the eye lens 99 without cavity 40. It follows that the eye lens 1 according to the fourth example embodiment shown here can achieve a higher refractive power than an eye lens 99 according to the prior art with the same external dimensions (such as the vertex distance between the front side and back side or between the corresponding surfaces 12, 22 of the eye lens 1).

This effect can be used to reduce the dimensions of the eye lens 1 in order to generate the same refractive power as exhibited by an eye lens 99 without cavity 40. This is depicted schematically in FIG. 4c. The curvatures of the cornea-facing and retina-facing surfaces 12, 22 of the lens elements 10, 20 are smaller. This results in smaller dimensions of the eye lens 1 according to a fifth example embodiment, shown here, compared to an eye lens 99 without cavity 40 but with the same focal length.

It should be noted that, in the fifth example embodiment, not only the curvature of the surfaces 12, 22, but additionally also the z-extent of the cavity 40 could have been adjusted in order to be able to generate the same focal length. Furthermore, it should be noted that, in the two example embodiments four and five, the extent of the opening 50 in the z-direction is less than the extent of the cavity 40 in the z-direction; however, this is irrelevant for the considerations relating to the refractive power and the reduction of the volume of the eye lens 1.

Figures 5, 6A, 6B, 6C:
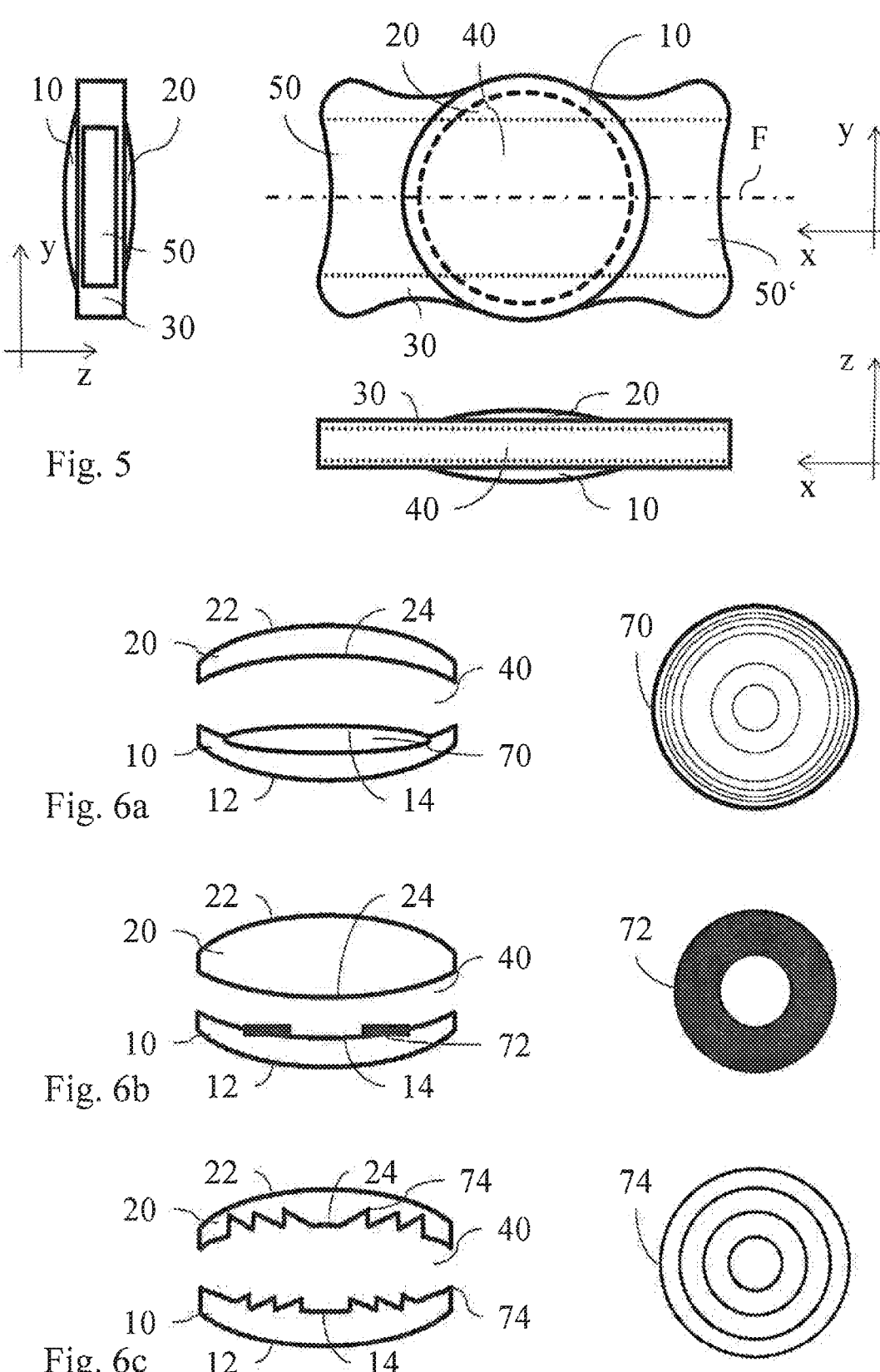
FIG. 5 are schematic illustrations of a sixth example embodiment of an eye lens in a top view and in two side views.
FIGS. 6a, 6b and 6c are schematic illustrations for variants of the lens elements in a sectional plane and a top view of details of the lens elements.

FIG. 5 shows schematic illustrations of a sixth example embodiment of an eye lens 1. The representations in the top view (top right) and the side views (left and bottom) correspond to those in FIG. 2. In the example embodiment shown here, the cavity 40 has two openings 50, 50'. The openings 50, 50' are on opposite sides of the cavity 40. In this example, the openings 50, 50' allow liquid to flow into the cavity 40 in the positive x-direction for opening 50' and in the negative x-direction for opening 50. The two side views show that the cavity 40 and the openings 50, 50' have the same z-extension. If an eye lens 1 shaped in this way is folded along the axis F, which is drawn in as a line of dots and dashes, the result is a particularly small volume of the eye lens 1 for an implantation.

It should be noted that, in the sixth example embodiment shown here, the intermediate element 30 comprises the haptics. This configuration of the intermediate element 30 is possible independently of the number of openings 50, 50'; the intermediate element 30 can also be shaped in this way in the other example embodiments shown. Furthermore, it should be noted that the embodiment shown here is particularly suitable for shaping the cavity 40 and the openings 50, 50' by application of an ablating process, by stamping or by casting the eye lens 1.

In all the example embodiments of the eye lens 1 shown so far, the two surfaces 14, 24 facing the cavity 40 have a planar shape. Variants for these surfaces 14, 24 are shown in FIGS. 6a to c. For this purpose, the front 10 and the back 20 lens element are shown schematically on the left in a section in the xz-plane. On the right-hand side, a detail of the configurations is shown in each case in a top view in an xy-plane. All variants shown here can find use on the front 10 and/or back 20 lens element in the various example embodiments.

FIG. 6a shows a back lens element 20 on the left, which has a curvature on the cavity-facing surface 24. The back lens element 20 is shaped here as a meniscus eye lens; it has a positive refractive power. FIG. 6a furthermore shows a front lens element 10 which comprises a further lens 70. In this case, the further lens 70 has a refractive index which differs from the rest of the front lens element 10 (or from the first optical region). The front lens element 10 is thus designed like a kit element and has a positive refractive power. Chromatic aberrations, for example, can be corrected particularly well in this way. The further lens 70 is shown in top view on the right-hand side. Here, the thin, concentric lines represent contour lines.

On the left, FIG. 6b depicts a front lens element 10 which comprises a stop 72. The stop 72 is designed to be annular, as depicted on the right in the figure. Light is blocked in the region of the stop 72. In the example shown, the perceived depth of field can be adjusted in this way. In this example, stop 72 is located on a curved cavity-facing surface 14; this surface could also be designed to be planar. The back lens element 20 is shaped here as a biconvex lens.

On the left, FIG. 6c shows a diffractive optical structure 74 on both surfaces 14, 24 facing the cavity 40. The diffractive optical structure 74 is designed to be rotationally symmetric, as depicted on the right in the figure. Here, the rims of the diffractive optical structure 74 are shown as rings in top view. The diffractive optical structure 74 of the two lens elements 10, 20 is in each case superimposed on a curved surface 14, 24; said diffractive optical structures could also be superimposed on a flat surface. In this case, the structures are placed onto the surface 14 or they are "missing" from the surface 24. In an example embodiment, only one of the front 10 and back 20 lens elements has a diffractive optical structure 74. The structures 74 shown allow more than one refractive power to be provided.

FIGS. 7a and b show schematic illustrations of a seventh example embodiment in two different sectional planes. In this case, the sectional planes correspond to those from FIGS. 3a and b. In this example embodiment, the surface 14 of the front lens element 10 facing the cavity 40 has a spherical-toric shape. In the yz-plane shown in FIG. 7a, the surface 14 has a spherical shape with a curvature that deviates from the curvature in the xz-plane depicted in FIG. 7b. An aspherical-toric shape is likewise possible. The surface 24 of the back lens element 20 facing the cavity 40 has a cylindrical shape: In the xz-plane shown in FIG. 7b, the surface 24 has a spherical shape with a finite curvature while the curvature in the yz-plane depicted in FIG. 7a has an infinite radius of curvature.

It is also possible for only one of the surfaces 14, 24 facing the cavity to have a toric shape. Each of the two configurations of the lens elements 10, 20 shown may also occur in any of the other example embodiments discussed.

FIG. 8 shows schematic illustrations of an eighth example embodiment. In this case, the surfaces 14, 24 of the lens elements 10, 20 facing the cavil 40 have a cylindrical shape: The aforementioned surfaces 14, 24 have no curvature in a y-plane representation, while they have curvature in an xz-plane representation. An eye lens 1 shaped in this way is suitable for correcting astigmatism. In the depicted example embodiment, the cavity 40 has two openings 50, 50'. However—deviating from the sixth example embodiment depicted in FIG. 5—these are not oriented in the direction of the haptics, but are aligned perpendicularly thereto. In this way, the stability of the haptic is not affected. If an eye lens 1 shaped in this way is folded along the axis F, which is drawn in as a line of dots and dashes, the result is a particularly small volume of the eye lens 1 for an implantation. The embodiment shown here is particularly suitable for shaping the cavity 40 and the openings 50, 50' using an ablating method such as drilling, or for stamping or casting the eye lens 1.

FIG. 9 shows a schematic illustration of the lens elements 10, 20 for a variant of the eye lens 1 with a clear, hydrophilic gel 90 in the cavity 40. This gel 90 can be introduced into the cavity 40 following an implantation of the eye lens 1. In this case, the gel 90 is chosen so that it additionally stabilizes the eye lens 1 in the hydrated state. Here, the gel 90 has a higher refractive index than that of aqueous humor. As a result, the total refractive power of the eye lens 1 is increased compared to an eye lens of the same geometry without gel 90. The gel 90 could also have a refractive index greater than that of the material of the lens elements 10, 20. In that case the total refractive power would be even greater.

In this case, the aforementioned features of the invention, which are described in various example embodiments, can be used not only in the specified example combinations but also in other combinations or on their own, without departing from the scope of the present invention.

A description of a piece of equipment relating to method features is analogously applicable to the corresponding method with respect to these features, while method features correspondingly represent functional features of the equipment described.

The invention claimed is:

1. A non-accommodating intraocular lens (IOL) that is implantable in an eye, comprising:
   a front lens element having a first optical region and a first positive refractive power;
   a back lens element having a second optical region and a second positive refractive power;
   an intermediate element,
   wherein the intermediate element is connected to the front lens element outside of the first optical region and wherein the intermediate element is connected to the back lens element outside of the second optical region, so that the front lens element, the back lens element, and the intermediate element together form a cavity,
   wherein the intermediate element fixedly spaces the front lens element from the back lens element when the eye lens is implanted,
   wherein an opening extends into the cavity to allow liquid to flow into the cavity,
   wherein a thickness of the eye lens measured as a maximum extent along a z axis is less than 3.0 mm, and
   wherein each of the first positive refractive power and the second positive refractive power are fixed.

2. The IOL as claimed in claim 1, wherein the front lens element and the back lens element are configured to allow the IOL to be folded.

3. The IOL as claimed in claim 1, wherein the thickness of the IOL is less than 1.5 mm.

4. The IOL as claimed in claim 1, wherein the thickness of the IOL is less than 0.9 mm.

5. The IOL as claimed in claim 1, wherein a surface which is part of at least one of the front lens element or the back lens element and faces the cavity comprises a coating which mitigates the front lens element and the back lens element sticking together.

6. The IOL as claimed in claim 1, wherein a surface which is part of at least one of the front lens element or the back lens element and faces the cavity comprises at least one of a stop or a diffractive optical structure.

7. The IOL as claimed in claim 1, wherein at least one of the front lens element or the back lens element has exactly two optically effective surfaces.

8. The IOL as claimed in claim 1, wherein at least one of the front lens element or the back lens element has an optically effective surface, wherein the optically effective surface is toric in shape.

9. The IOL as claimed in claim 1, wherein at least one of the front lens element or the back lens element has an optically effective surface facing the cavity, wherein the optically effective surface is toric in shape.

10. The IOL as claimed in claim 1, wherein the IOL is formed in one piece.

11. The IOL as claimed in claim 1, wherein the cavity contains a clear hydrophilic gel following an implantation of the IOL into an eye.

12. A method for implanting an IOL as claimed in claim 11, comprising:

inserting the IOL into the eye; and introducing a clear hydrophilic gel into the cavity.

13. A method for producing an IOL as claimed in claim 1, comprising shaping the cavity with the opening using a process selected from a group consisting of: selective laser etching, ablating a lens material, punching, shaping by ion implantation, casting, bracing, and any combination thereof.

14. The IOL as claimed in claim 1, wherein the front lens element, the back lens element and the intermediate element have a stiffness such that the IOL is minimally deformed by forces typically encountered by the IOL when the IOL is in situ following implantation in the eye.

15. The IOL as claimed in claim 14, wherein the front lens element, the back lens element and the intermediate element have the stiffness such that when the IOL is in situ following implantation in the eye a distance between the front lens element and the back lens element changes by an amount selected from a group consisting of less than 20%, less than 10% and less than 5%.

\* \* \* \* \*